United States Patent
Yokogi et al.

(10) Patent No.: US 11,058,620 B2
(45) Date of Patent: *Jul. 13, 2021

(54) PRODUCT COMPOSITION COMPRISING A DISCRETE PARTICLE AND AN AQUEOUS BASE COMPOSITION

(71) Applicant: The Procter & Gamble Company, Cincinnati, OH (US)

(72) Inventors: Junichi Yokogi, Singapore (SG); XinHao Zhu, Singapore (SG); Jorge Max Sunkel, West Chester, OH (US)

(73) Assignee: The Procter and Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/441,618

(22) Filed: Jun. 14, 2019

(65) Prior Publication Data

US 2019/0290553 A1    Sep. 26, 2019

Related U.S. Application Data

(63) Continuation of application No. PCT/US2018/027405, filed on Apr. 13, 2018.

(60) Provisional application No. 62/484,912, filed on Apr. 13, 2017, provisional application No. 62/484,915, filed on Apr. 13, 2017, provisional application No. 62/484,917, filed on Apr. 13, 2017, provisional application No. 62/484,918, filed on Apr. 13, 2017, provisional application No. 62/484,919, filed on Apr.

(Continued)

(51) Int. Cl.

| | | |
|---|---|---|
| *A61K 8/02* | (2006.01) | |
| *A61K 8/04* | (2006.01) | |
| *A61K 8/34* | (2006.01) | |
| *A61K 8/41* | (2006.01) | |
| *A61K 8/42* | (2006.01) | |
| *A61K 8/46* | (2006.01) | |
| *A61Q 5/12* | (2006.01) | |
| *A61K 8/44* | (2006.01) | |
| *A61K 8/49* | (2006.01) | |
| *A61K 8/58* | (2006.01) | |
| *A61K 8/898* | (2006.01) | |
| *A61K 8/26* | (2006.01) | |
| *A61K 8/19* | (2006.01) | |
| *A61K 8/84* | (2006.01) | |
| *A61K 8/86* | (2006.01) | |
| *A61K 8/87* | (2006.01) | |
| *A61Q 5/02* | (2006.01) | |
| *A61K 8/60* | (2006.01) | |
| *A61K 8/81* | (2006.01) | |
| *A61K 8/90* | (2006.01) | |
| *A61K 8/25* | (2006.01) | |
| *A61K 8/368* | (2006.01) | |

(52) U.S. Cl.
CPC ............ *A61K 8/416* (2013.01); *A61K 8/0241* (2013.01); *A61K 8/04* (2013.01); *A61K 8/042* (2013.01); *A61K 8/044* (2013.01); *A61K 8/19* (2013.01); *A61K 8/25* (2013.01); *A61K 8/26* (2013.01); *A61K 8/34* (2013.01); *A61K 8/342* (2013.01); *A61K 8/347* (2013.01); *A61K 8/368* (2013.01); *A61K 8/42* (2013.01); *A61K 8/44* (2013.01); *A61K 8/442* (2013.01); *A61K 8/463* (2013.01); *A61K 8/49* (2013.01); *A61K 8/585* (2013.01); *A61K 8/60* (2013.01); *A61K 8/81* (2013.01); *A61K 8/8152* (2013.01); *A61K 8/84* (2013.01); *A61K 8/86* (2013.01); *A61K 8/87* (2013.01); *A61K 8/898* (2013.01); *A61K 8/90* (2013.01); *A61Q 5/02* (2013.01); *A61Q 5/12* (2013.01); *A61K 2800/30* (2013.01); *A61K 2800/41* (2013.01); *A61K 2800/43* (2013.01); *A61K 2800/592* (2013.01); *A61K 2800/596* (2013.01); *A61K 2800/652* (2013.01); *A61K 2800/805* (2013.01)

(58) Field of Classification Search
None
See application file for complete search history.

(56) References Cited

U.S. PATENT DOCUMENTS

| | | |
|---|---|---|
| 4,275,055 A | 6/1981 | Nachtigal |
| 4,795,327 A | 1/1989 | Gaylord |
| | (Continued) | |

FOREIGN PATENT DOCUMENTS

| | | |
|---|---|---|
| EP | 0446094 A1 | 9/1991 |
| EP | 0446094 B1 | 3/1995 |
| | (Continued) | |

OTHER PUBLICATIONS

U.S. Appl. No. 16/595,755, filed Oct. 8, 2019, Yokogi et al.
U.S. Appl. No. 16/432,371, filed Jun. 5, 2019, Brown et al.
All final and non-final office actions for U.S. Appl. No. 10/454,433.
All final and non-final office actions for U.S. Appl. No. 11/228,770.
All final and non-final office actions for U.S. Appl. No. 11/475,484.
All final and non-final office actions for U.S. Appl. No. 11/475,485.
All final and non-final office actions for U.S. Appl. No. 11/602,525.

(Continued)

*Primary Examiner* — Brian Gulledge
(74) *Attorney, Agent, or Firm* — Angela K. Haughey

(57) ABSTRACT

Disclosed is a product composition comprising: a discrete particle of a mixture composition, wherein the mixture composition comprises a surfactant and a high melting point fatty compound and a benefit agent; and an aqueous base composition comprising a surfactant, a high melting point fatty compound, and an aqueous carrier, and wherein the aqueous base composition is substantially free of detersive surfactant. The product composition of the present invention provides at least one the followings: more flexibility in the product composition rheology; improved stability in the product composition; improved deposition of benefit agents; and improved visual/aesthetic appearance.

11 Claims, No Drawings

Related U.S. Application Data 13, 2017, provisional application No. 62/484,920, filed on Apr. 13, 2017, provisional application No. 62/532,365, filed on Jul. 14, 2017, provisional application No. 62/532,366, filed on Jul. 14, 2017, provisional application No. 62/532,368, filed on Jul. 14, 2017, provisional application No. 62/532,369, filed on Jul. 14, 2017, provisional application No. 62/532,371, filed on Jul. 14, 2017, provisional application No. 62/532,372, filed on Jul. 14, 2017.

(56) References Cited

U.S. PATENT DOCUMENTS

| | | | |
|---|---|---|---|
| 4,891,214 | A | 1/1990 | Stevens |
| 5,876,705 | A | 3/1999 | Uchiyama |
| 5,904,932 | A * | 5/1999 | De Vringer ............ A61K 8/347 424/450 |
| 5,955,066 | A | 9/1999 | Sako |
| 5,985,255 | A | 11/1999 | Vanlerberghe |
| 6,719,967 | B1 | 4/2004 | Brown |
| 6,878,368 | B2 | 4/2005 | Ohta |
| 7,303,744 | B2 | 12/2007 | Wells |
| 8,017,108 | B2 | 9/2011 | Baker |
| 8,349,301 | B2 | 1/2013 | Wells |
| 8,349,302 | B2 | 1/2013 | Johnson |
| 8,361,448 | B2 | 1/2013 | Johnson |
| 8,361,449 | B2 | 1/2013 | Wells |
| 8,361,450 | B2 | 1/2013 | Johnson |
| 8,367,048 | B2 | 2/2013 | Wells |
| 8,470,305 | B2 | 6/2013 | Johnson |
| 9,539,444 | B2 | 1/2017 | Kinoshita |
| 10,751,272 | B2 | 8/2020 | Yokogi |
| 2003/0008790 | A1 | 1/2003 | Carew |
| 2003/0103923 | A1 | 6/2003 | Ohta |
| 2003/0113354 | A1 | 6/2003 | Schmid |
| 2003/0223952 | A1 | 12/2003 | Wells |
| 2009/0324532 | A1 | 12/2009 | Okada |
| 2010/0143280 | A1 | 6/2010 | Yokogi |
| 2013/0071346 | A1 | 3/2013 | Okada |
| 2015/0093420 | A1 | 4/2015 | Snyder |
| 2016/0095808 | A1 * | 4/2016 | Okada ................. A61K 8/0216 424/401 |
| 2016/0143827 | A1 | 5/2016 | Castan Barberan |
| 2017/0326060 | A1 | 11/2017 | Matsuo |
| 2019/0290554 | A1 | 9/2019 | Yokogi |
| 2019/0290555 | A1 | 9/2019 | Yokogi |
| 2019/0290556 | A1 | 9/2019 | Yokogi |
| 2019/0290562 | A1 | 9/2019 | Yokogi |
| 2019/0290567 | A1 | 9/2019 | Yokogi |
| 2019/0290568 | A1 | 9/2019 | Yokogi |
| 2019/0307665 | A1 | 10/2019 | Yokogi |
| 2019/0365611 | A1 | 12/2019 | Brown et al. |
| 2020/0113796 | A1 | 4/2020 | Yokogi |

FOREIGN PATENT DOCUMENTS

| | | |
|---|---|---|
| EP | 1779838 A1 | 5/2007 |
| EP | 1337231 B1 | 8/2007 |
| JP | 2000355519 A | 12/2000 |
| WO | 2014014053 A1 | 1/2014 |
| WO | WO2016067740 A1 | 5/2016 |
| WO | WO2018191573 A1 | 10/2018 |

OTHER PUBLICATIONS

All final and non-final office actions for U.S. Appl. No. 11/602,705.
All final and non-final office actions for U.S. Appl. No. 11/952,380.
All final and non-final office actions for U.S. Appl. No. 12/040,980.
All final and non-final office actions for U.S. Appl. No. 13/411,992.
PCT International Search Report and Written Opinion for PCT/US2018/027403 dated Jun. 13, 2018.
PCT International Search Report and Written Opinion for PCT/US2018/027404 dated Jun. 13, 2018.
PCT International Search Report and Written Opinion for PCT/US2018/027405 dated Jun. 13, 2018.
PCT International Search Report and Written Opinion for PCT/US2018/027406 dated Jul. 4, 2018.
PCT International Search Report and Written Opinion for PCT/US2018/027407 dated Jul. 4, 2018.
PCT International Search Report and Written Opinion for PCT/US2018/027408 dated Jul. 4, 2018.
PCT International Search Report and Written Opinion for PCT/US2018/027409 dated Jun. 29, 2018.
PCT International Search Report and Written Opinion for PCT/US2018/027410 dated Jun. 29, 2018.
"Cleansing Pack" Mintel Database, www.gnpd.com, Apr. 6, 2018.
"Conditioner Soap Bar" Mintel Database, www.gnpd.com, Feb. 15, 2018.
"Hydrating Conditioner Bar" Mintel Database, www.gnpd.com, Aug. 1, 2018.
PCT International Search Report and Written Opinion for PCT. US2019/055284 dated Jan. 22, 2020.
All final and non-final office actions for U.S. Appl. No. 16/441,639.
All final and non-final office actions for U.S. Appl. No. 16/441,671.
All final and non-final office actions for U.S. Appl. No. 16/441,588.
All final and non-final office actions for U.S. Appl. No. 16/441,604.
All final and non-final office actions for U.S. Appl. No. 16/441,650.
All final and non-final office actions for U.S. Appl. No. 16/441,662.
All final and non-final office actions for U.S. Appl. No. 16/441,686.

* cited by examiner

PRODUCT COMPOSITION COMPRISING A DISCRETE PARTICLE AND AN AQUEOUS BASE COMPOSITION

FIELD OF THE INVENTION

The present invention relates to a product composition comprising: a discrete particle of a mixture composition, wherein the mixture composition comprises a surfactant and a high melting point fatty compound and a benefit agent; and an aqueous base composition comprising a surfactant, a high melting point fatty compound, and an aqueous carrier, and wherein the aqueous base composition is substantially free of detersive surfactant. The product composition of the present invention provides at least one the followings: more flexibility in the product composition rheology; improved stability in the product composition; improved deposition of benefit agents; and improved visual/aesthetic appearance.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits.

For example, United States Patent Application Publication No. 2003/0103923 from SAN-EI KAGAKU relates to a composition containing an alcohol, the composition being for blending in a hair treatment agent, and hair conditioners prepared from the hair treatment agents. SAN-EI publication discloses a variety of such compositions for blending in hair treatment agents, including compositions containing fatty alcohols and cationic surfactants, for example, in Examples 100-110. The SAN-EI publication also discloses hair conditioners by using such compositions for blending, for example, in Example 112-118.

In Examples 112-117 of the SAN-EI publication, the compositions for blending (Examples 102, 103, 104 and 106) are heated up to 80° C. or more, then mixed with mainly water to make hair conditioners. The compositions for blending (Examples 102, 103, 104 and 106) used therein contain higher percentages of liquid material (for example, 27% propylene glycol in Example 102, 47% of liquid petrolatum in Example 103, 43% of glycerin and 18% of liquid petrolatum in Example 104, and 28% of glycerin in Example 106) together with fatty alcohols and cationic surfactants.

In Example 118 of the SAN-EI publication, a composition for blending (Example 111) is added to an emulsion cooled down below 40° C., wherein the emulsion is of water and an additive composition containing a cationic surfactant and a fatty alcohol, and further mixed with water to make hair conditioner. The composition for blending (Example 111) contains ethanol, cationic surfactant, and more than 80% of water, and no fatty alcohols.

SAN-EI publication also discloses preparation of hair conditioners in Examples 150-156. In Example 150-154, compositions for blending (Examples 123, 126, 127, 130, 133, and 134) are heated to above 80° C., and added to water which is also heated to above 80° C., and emulsified and cooled to make hair conditioners. The compositions for blending (Examples 123, 126, 127, 130, 133, and 134) contain cationic surfactants and fatty alcohols, and also 15-20% of liquid oils (in Examples 123, 130 and 133) or 6-8% of polyoxyethylene esters (in Examples 126, 127 and 134).

Another example can be United States Patent Application Publication No. 2003/223952 from P&G relating to a process for preparing cleansing composition comprising (a) combining a fatty alcohol and a surfactant in a premix at a temperature sufficient to allow partitioning of the surfactant into the fatty alcohol, (b) cooling the mixture below the chain melt temperature of the premix to form a gel network, (c) adding the gel network to a detersive surfactant and an aqueous carrier to form a cleansing composition. The P&G publication discloses Examples in paragraphs [0186]-[0190], using such gel network containing fatty alcohol and cationic surfactant.

Also, United States Patent Application Publication No. 2016/143827 from Kao discloses a composition that is solid at room temperature and wherein the water content is 10 wt % or less, and a hair conditioner composition prepared by dispersing the solid composition in water at moderate temperatures. European Patent Application Publication No. 2394632 from Shiseido discloses a hair conditioner composition with an extremely low water content, and from which a hair conditioner composition can easily be manufactured simply by diluting with water.

However, there remains a need for conditioning compositions to provide at least one of the followings:
  More flexibility in product composition rheology especially storage modulus (G'), preferably even when using the same amounts of actives such as surfactants and high melting point fatty compounds, and also preferably providing such flexibility independently from the use of thickening polymer. Product compositions having different rheology especially storage modulus (G') are believed to provide different moundness, and product composition having a higher moundness tends to provide rich conditioning perception/feeling and also tends to be easy to apply to hair and/or easy to hold on palm.
  Improved stability of aqueous base compositions and product compositions, especially when using smaller amounts of actives such as surfactants and high melting point fatty compounds in aqueous base compositions, and preferably providing such stability improvement independently from the use of thickening polymer.
  Improved deposition of benefit agents when containing benefit agents in the composition;
  Improved stability when containing incompatible components;
  Improved visual/aesthetic appearance.
  None of the existing art provides all of the advantages and benefits of the present invention.

SUMMARY OF THE INVENTION

The present invention is directed to a product composition comprising:
a discrete particle of a mixture composition, wherein the mixture composition comprises a surfactant, a high melting point fatty compound, and a benefit agent other than the surfactant and the high melting point fatty compound; and
an aqueous base composition comprising a surfactant, a high melting point fatty compound, and an aqueous carrier, and wherein the aqueous base composition is substantially free of detersive surfactant.

The product composition of the present invention provides at least one the followings: more flexibility in the product composition rheology; improved stability in the product composition; improved deposition of benefit agents; and improved visual/aesthetic appearance.

These and other features, aspects, and advantages of the present invention will become better understood from a reading of the following description, and appended claims.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Mixture Composition

The mixture composition herein comprises a surfactant and a high melting point fatty compound. The mixture composition useful herein further contains a benefit agent. These ingredients are explained later in detail. The mixtures composition are contained in the product composition at a level by weight of the product composition, of preferably from about 0.01% to about 70%, more preferably from about 0.01% to about 50%, still more preferably from about 0.05% to about 30%, in view of having discrete particles of the mixture composition in the aqueous base composition and in the product composition, and also in view of providing at least one the followings: more flexibility in the product composition rheology; improved stability in the product composition; improved deposition of benefit agents; and improved visual/aesthetic appearance.

When the mixture compositions contain benefit agents and such benefit agents are silicones and/or perfumes, the mixture compositions may be contained in the product composition at a level by weight of the product composition, of preferably from about 0.1% to about 70%, more preferably from about 0.5% to about 50%, still more preferably from about 1% to about 30%, even more preferably from about 2% about 20%.

When the mixture compositions contain benefit agents and such benefit agents are coloring agents and/or mica, the mixture compositions may be contained in the product composition at a level by weight of the product composition, of preferably from about 0.01% to about 50%, and more preferably from about 0.01% to about 30%, still more preferably from about 0.01% to about 20%, even more preferably from about 0.05% to about 10%.

The surfactants and the high melting point fatty compounds are present in the mixture composition, with or without other ingredients, at a level by weight of the mixture composition of, preferably from about 10% to about 99.9%, more preferably from about 20% to about 99.9%, still more preferably from about 40% to about 99.9%, even more preferably from about 60% to about 99.9%, further more preferably from about 80% to about 99.9%, in view of having discrete particles of the mixture composition in the aqueous base composition and in the product composition while containing other ingredients such as benefit agents, and also in view of providing at least one the followings: more flexibility in the product composition rheology; improved stability in the product composition; improved deposition of benefit agents; and improved visual/aesthetic appearance.

Other than the surfactants and high melting point fatty compounds, when the mixture composition contains any liquid such as water-insoluble, water-miscible, and water-soluble liquids and water, it is also preferred to control the level of such liquids, so that the total liquid level in the mixture composition can be up to about 92%, up to about 60%, more preferably up to about 50%, still more preferably up to about 40%, even more preferably up to about 30% by weight of the mixture composition, in view of having discrete particle of the mixture composition in the aqueous base composition and in the product composition.

When the liquid is water insoluble liquid such as silicones, such water insoluble liquid can be contained in the mixture composition at a level by weight of the mixture composition of preferably up to about 90%, up to about 60%, more preferably up to about 50%, still more preferably up to about 40%, even more preferably up to about 30%.

When the liquid is water miscible liquid such propylene glycol and glycerin, such water miscible liquid can be contained in the mixture composition at a level by weight of the mixture composition of preferably up to about 90%, up to about 60%, more preferably up to about 50%, still more preferably up to about 40%, even more preferably up to about 30%.

When the liquid is water soluble liquids such as isopropylalcohol (IPA) and ethanol, such water soluble liquid can be contained in the mixture composition at a level by weight of the mixture composition of preferably up to about 50%, more preferably up to about 30%, still more preferably up to about 20%.

When the mixture composition contains water, it is preferred to control the level of the water so that the mixture composition contains less than about 50% of water, more preferably less than about 25%, still more preferably less than about 15%, even more preferably less than about 10%, further preferably less than about 8% of water, by weight of the mixture composition, in view of having discrete particle of the mixture composition in the aqueous base composition and in the product composition.

Preferably in the mixture composition, the surfactant and the high melting point fatty compound are contained at a level such that the weight ratio of the surfactant to the high melting point fatty compound is in the range of from about 1:1 to about 1:10, more preferably from about 1:1 to about 1:4, still more preferably from about 1:2 to about 1:4, in view of providing rheology and/or conditioning benefit.

Surfactant for the Mixture Composition

The surfactant used for the mixture composition is preferably hydrophobic, and is also preferably selected from the group consisting of: a cationic surfactant, a nonionic surfactant, and mixtures thereof; and still more preferably a cationic surfactant. Such preferred cationic surfactants are further explained below under the title "CATIONIC SURFACTANT".

High Melting Point Fatty Compound for the Mixture Composition

The high melting point fatty compound used for the mixture composition is explained below under the title "HIGH MELTING POINT FATTY COMPOUND".

Benefit Agent for the Mixture Composition

The mixture composition further comprises a benefit agent in addition to the surfactant and the high melting point fatty compound, which are different from the surfactant and the high melting point fatty compound. This benefit agent is also different from the aqueous carrier and water which may be contained in the mixture composition.

The benefit agent can be contained in the mixture composition at a level by the weight of the mixture composition, of preferably from about 0.1% to about 90%, more preferably from about 0.3% to about 60%, still more preferably from about 0.5% to about 40%, even more preferably from about 0.5% to about 30% in view of providing benefits from the benefit agents and in view of having discrete particle of the mixture composition in the aqueous composition and in the product composition.

Preferably, such benefit agent is selected from the group consisting of silicone compounds, perfumes, coloring agents to add a different color to the discrete particle from the color of the aqueous base composition, incompatible agents which are incompatible to at least one ingredient contained in the aqueous base composition, and mixtures thereof.

Such silicone compounds are further explained below under the title "SILICONE COMPOUND".

Such perfumes can be anything, for example, perfume per se, and perfume micro capsule (PMC) in which perfume is encapsulated by a polymeric outer layer.

Such coloring agent can be anything, for example, pigments and dyes.

Such incompatible agents are, for example, those selected from the group consisting of: solid minerals or chemical substances that have high ionic strength and/or high surface charge and tend to cause agglomeration and/or crystallization, which are, for example, mica, salicylic acid, and metal pyrithione such as zinc pyrithione with or without ionic polymer coating or dispersion; organic oil material which is highly interactive with gel network component, for example, Hexyl Decanol, Isostearyl Isostearate; and mixtures thereof.

Depending on the type of the benefit agent, when containing the benefit agent, the product composition may provide at least one of the following:
   Improved deposition of benefit agents;
   Improved stability when containing incompatible agents;
   Improved visual/aesthetic appearance when containing coloring agents to add a different color to the discrete particle from the color of the aqueous base composition.

Aqueous Base Composition

The aqueous base composition can be included in the product composition at a level of q.s. to 100% by weight of the product composition, preferably from about 30% to about 99.9%, more preferably from about 50% to about 99.9%, still more preferably from about 70% to about 99.9%, even more preferably from about 80% to about 99.9%, further more preferably from about 90% to about 99.9% by weight of the product composition, in view of having discrete particles of the mixture composition in the aqueous base composition and in the product composition.

The aqueous base compositions of the present invention comprise a surfactant. The surfactant can be included in the aqueous base composition at a level of preferably from about 0.1% to about 10%, more preferably from about 0.3% to about 8%, still more preferably from about 0.5% to about 5%, even more preferably from about 0.7% to about 4% by weight of the aqueous base composition, in view of providing conditioning benefits.

The aqueous base compositions of the present invention comprise a high melting point fatty compound. The high melting point fatty compound can be included in the aqueous base composition at a level of preferably from about 0.5% to about 15%, more preferably from about 1.0% to about 10%, still more preferably from about 1.5% to about 8.0%, even more preferably from about 2.0% to about 6.0%, further more preferably from about 2.5% to about 6.0% by weight of the aqueous base composition, in view of providing conditioning benefits.

The aqueous base compositions of the present invention comprise an aqueous carrier. Generally, the aqueous carrier can be contained in the aqueous base compositions at a level of q.s. to 100% of the aqueous base composition, preferably from about 40% to about 99%, more preferably from about 50% to about 95%, still more preferably from about 70% to about 95%, even more preferably from about 80% to about 95% by weight of the aqueous base composition.

Preferably in the aqueous base composition, the surfactant and the high melting point fatty compound are contained at a level such that the weight ratio of the surfactant to the high melting point fatty compound is in the range of from about 1:1 to about 1:10, more preferably from about 1:1 to about 1:4, still more preferably from about 1:2 to about 1:4, in view of providing rheology and/or conditioning benefit.

Surfactant for the Aqueous Base Composition

The surfactant used for the aqueous base composition is preferably hydrophobic, and is also preferably selected from the group consisting of: a cationic surfactant, a nonionic surfactant, and mixtures thereof; and still more preferably a cationic surfactant. Such preferred cationic surfactants are further explained below under the title "CATIONIC SURFACTANT".

The aqueous base composition is preferably substantially free of detersive surfactants, which is explained below in detail under the title "SUBSTANTIALLY FREE OF DETERSIVE SURFACTANT".

High Melting Point Fatty Compound for the Aqueous Base Composition

The high melting point fatty compound used for the aqueous base composition is explained below under the title "HIGH MELTING POINT FATTY COMPOUND".

Benefit Agent for the Aqueous Base Composition

The aqueous base composition may further comprise a benefit agent in addition to the surfactant and the high melting point fatty compound, which are different from the surfactant and the high melting point fatty compound. This benefit agent is also different from the aqueous carrier and water.

The benefit agent can be contained in the aqueous base composition at a level by the weight of the aqueous base composition, of preferably from about 0.05% to about 60%, more preferably from about 0.1% to about 30%, still more preferably from about 0.1% to about 20%, even more preferably from about 0.1% to about 10%, in view of providing benefits from the benefit agents, and in view of not deteriorating the benefit from the aqueous base composition especially the surfactant and high melting point fatty compound.

The benefit agent can be contained in the aqueous base composition, so that the benefit agent can be contained in the product composition at a level by the weight of the product composition, of preferably from about 0.05% to about 30%, more preferably from about 0.1% to about 15%, still more preferably from about 0.1% to about 10%, even more preferably from about 0.1% to about 7%, in view of providing benefits from the benefit agents, and in view of not deteriorating the benefit from the aqueous base composition especially the surfactant and high melting point fatty compound.

Preferably, such benefit agents used in the aqueous base composition are selected from the group consisting of: silicone compounds, perfumes, incompatible agents which are incompatible to at least one ingredient contained in the mixture composition and/or in the discrete particle, and mixtures thereof. More preferably, such benefit agents used in the aqueous base composition are incompatible agents which are incompatible to at least one ingredient contained in the mixture composition and/or in the discrete particle.

Such silicone compounds are further explained below under the title "SILICONE COMPOUND".

Such perfumes can be anything, for example, perfume per se, and perfume micro capsule (PMC) in which perfume is encapsulated by a polymeric outer layer.

Such incompatible agents are, for example, those selected from the group consisting of: solid minerals or chemical substances that have high ionic strength and/or high surface charge and tend to cause agglomeration and/or crystallization, which are, for example, mica, and metal pyrithione such as zinc pyrithione with or without ionic polymer coating or dispersion; organic oil material which is highly interactive with gel network component, for example, Hexyl Decanol, Isostearyl Isostearate;

and mixtures thereof.

Depending on the type of the benefit agent, when containing the benefit agent, the product composition may provide at least one of the following:

Improved deposition of benefit agents;

Improved stability when containing incompatible agents.

Discrete Particle

The product composition comprises discrete particles of the mixture composition. The discrete particles herein are those dispersed in the aqueous base composition and can be observed as discrete particle in final product composition visually, for example, by microscope, however, those do not show maltese cross sign when measured by polarized light microscopy. This means that the discrete particles useful herein are not vesicles which are often seen in emulsions such as aqueous base composition comprising surfactants, high melting fatty compounds and aqueous carrier. Generally, surfactants, high melting fatty compounds and aqueous carrier form emulsions, preferably a gel matrix. In such emulsions and gel matrix, these components often form lamellar vesicle and/or lamellar sheet. Such Lamellar vesicle can be observed as discrete particle by microscope, however, shows maltese cross sign when measured by polarized microscope.

The discrete particles are contained in the product composition at a level by weight of the product composition, of preferably from about 0.1% to about 70%, more preferably from about 0.1% to about 50%, still more preferably from about 0.1% to about 30%, in view of providing at least one the followings: more flexibility in the product composition rheology; improved stability in the product composition; improved deposition of benefit agents; and improved visual/aesthetic appearance.

The discrete particle is preferably swollen in the product composition, more preferably swollen by aqueous carrier, still more preferably by water. The discrete particle can be swollen in the aqueous base composition by the aqueous carrier and/or water from the aqueous base composition. Alternatively or concurrently, the discrete particle can be swollen before mixing it with the aqueous base composition, for example, when or after preparing the discrete particle from the mixture composition, by using an aqueous carrier and/or water as a solvent to disperse discrete particle. Such solvents are considered as components of the aqueous base composition, when calculating the amount of the component.

It is believed that swelling of the discrete particle is saturated in about 3 days and up to 1 week at the longest regardless the particle size and regardless of benefit agents inside if included. And, it is believed that, if it happens, diffusion and/or collapsing of discrete particle will happens within 1 week and complete within 3 weeks at the longest. It is also believed that physical properties and benefits of the discrete particle may be changed during swelling, diffusion and/or collapsing, but will be stabilized and will not change after 3 weeks. Thus, the discrete particles useful herein exist in the composition preferably for 1 month or longer, more preferably 3 months or longer, still more preferably 6 months or longer, further more preferably for 12 month or longer, even more preferably for 24 month or longer. The swollen discrete particle preferably has a particle size of from about 1 micrometer to about 2000 micrometers, more preferably from about 10 micrometers to about 1000 micrometer, still more preferably from about 50 micrometers to about 500 micrometers. Such swollen discrete particles also can be observed as discrete particles by microscope, however, do not show maltese cross sign when measured by polarized light microscopy.

The discrete particles and the swollen discrete particles herein can be in any shape, for example, spherical shape, rectangular shape, or diamond shape.

Before swelling, preferably, the discrete particle is solid.

Before swelling, the discrete particle preferably comprises 100% of the mixture composition, i.e., consisting of the mixture composition. When the discrete particles contain water before swelling, it is preferred to control the level of the water before swelling, so that the discrete particle before swelling contains less than about 50% of water, more preferably less than about 25%, still more preferably less than about 15%, even more preferably less than about 10%, further preferably less than about 8% of water, by weight of the discrete particle.

Before swelling, the surfactants and the high melting point fatty compounds are present in the discrete particle, with or without other ingredients, at a level by weight of the discrete particle of, preferably from about 10% to about 100%, more preferably from about 20% to about 100%, still more preferably from about 40% to about 100%, even more preferably from about 60% to about 100%, further more preferably from about 80% to about 100%, in view of having discrete particles of the mixture composition in the aqueous base composition and in the product composition.

Before and after swelling, the discrete particle is preferably not an oil-in-water emulsion or water-in-oil-in-water emulsion, more preferably, not any emulsion including water-in-oil emulsion and oil-in-water-in-oil emulsion.

The discrete particle herein is different from particles coated or encapsulated by, for example, polymers.

The discrete particle useful herein is different from swellable silicone elastomer and swellable thickening polymer. Preferably, the discrete particle and the mixture composition are substantially free of such swellable silicone elastomer and swellable thickening polymer. In the present invention, "the discrete particle and the mixture composition being substantially free of swellable silicone elastomer and swellable thickening polymer" means that: the discrete particle and the mixture composition are free of swellable silicone elastomer and swellable thickening polymer; or, if the discrete particle and the mixture composition contains swellable silicone elastomer and swellable thickening polymer, the level of such swellable silicone elastomer and swellable thickening polymer is very low. In the present invention, a total level of such swellable silicone elastomer and swellable thickening polymer, if included, preferably 0.1% or less, more preferably 0.05% or less, still more preferably 0.01% or less by weight of the discrete particle or by the weight of the mixture composition. Most preferably, the total level of such swellable silicone elastomer and swellable thickening polymer is 0% by weight of the discrete particle or by the weight of the mixture composition.

2$^{nd}$ Discrete Particle

The product composition of the present invention may comprise 2$^{nd}$ discrete particle, in addition to the above discrete particle of the present invention which comprises the mixture comprising the surfactant, high melting point fatty alcohol, and benefit agent. The 2$^{nd}$ discrete particle useful herein comprises the mixture excluding the benefit agent, i.e., a mixture comprising a surfactant and a high melting point fatty compound. The components and the properties of the 2$^{nd}$ discrete particles are same as those described for the above discrete particle of the present invention, except for the inclusion of benefit agents.

Product Composition

The product composition comprises the discrete particles and the aqueous base composition, preferably consisting of the discrete particles and the aqueous base composition. The product composition of the present invention can be anything, and is preferably selected from the group consisting of a hair care product composition, a body care product composition, a facial skin care product composition, and mixtures thereof, more preferably a hair care product composition. Among the hair care compositions, still more preferred are hair conditioning compositions wherein the surfactants contained in the discrete particle and the aqueous composition are cationic surfactants.

Product Forms

The product compositions of the present invention can be in the form of rinse-off products or leave-on products, and can be formulated in a wide variety of product forms, including but not limited to creams, gels, emulsions, mousses and sprays. The product composition of the present invention is especially suitable for hair conditioners especially rinse-off hair conditioners.

When used as a rinse-off conditioner, the product composition is preferably used by the following steps:
(i) after shampooing hair, applying to the hair an effective amount of the conditioner composition for conditioning the hair; and
(ii) then rinsing the hair.

Effective amount herein is, for example, from about 0.1 ml to about 2 ml per 10 g of hair, preferably from about 0.2 ml to about 1.5 ml per 10 g of hair.

Cationic Surfactant

Cationic surfactant useful herein can be one cationic surfactant or a mixture of two or more cationic surfactants. Preferably, the cationic surfactant is selected from: mono-long alkyl quaternized ammonium salt; a combination of mono-long alkyl quaternized ammonium salt and di-long alkyl quaternized ammonium salt; mono-long alkyl amine; a combination of mono-long alkyl amine and di-long alkyl quaternized ammonium salt.

Mono-Long Alkyl Quaternized Ammonium Salt

The mono-long alkyl quaternized ammonium salts useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts are preferably combined with a mono-long alkyl quaternized ammonium salt or mono-long alkyl amine salt, at the weight ratio of from 1:1 to 1:5, more preferably from 1:1.2 to 1:5, still more preferably from 1:1.5 to 1:4, in view of stability in rheology and conditioning benefits.

Di-long alkyl quaternized ammonium salts useful herein are those having two long alkyl chains of from 12 to 30 carbon atoms, more preferably from 16 to 24 carbon atoms, still more preferably from 18 to 22 carbon atoms. Such di-long alkyl quaternized ammonium salts useful herein are those having the formula (I):

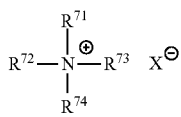

(I)

wherein two of $R^{71}$, $R^{72}$, $R^{73}$ and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Such preferred di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Mono-Long Alkyl Amine

Mono-long alkyl amine useful herein are those having one long alkyl chain of preferably from 12 to 30 carbon atoms, more preferably from 16 to 24 carbon atoms, still more preferably from 18 to 22 alkyl group. Mono-long alkyl amines useful herein also include mono-long alkyl amido-amines Primary, secondary, and tertiary fatty amines are useful.

Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethyl amine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethyl amine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines are used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid, at a molar ratio of the amine to the acid of from about 1:0.3 to about 1:2, more preferably from about 1:0.4 to about 1:1.

High Melting Point Fatty Compound

The compositions of the present invention comprise the high melting point fatty compound. By the use of high melting point fatty compound, the composition of the present invention provides improved conditioning benefits such as friction reduction during conditioner application, ease of spreading, and/or ease of detangling, compared to compositions containing no high melting point fatty compounds and/or compared to compositions containing low melting point fatty compounds instead of high melting point fatty compounds. By the use of high melting point fatty compound, the composition of the present invention may provide improved stability of the composition such as reduced the risk of phase separation, compared to compositions containing no high melting point fatty compounds and/or compared to compositions containing low melting point fatty compounds instead of high melting point fatty compounds.

The high melting point fatty compound useful herein have a melting point of 25° C. or higher, preferably 40° C. or higher, more preferably 45° C. or higher, still more preferably 50° C. or higher, in view of stability of the emulsion especially the gel matrix. Preferably, such melting point is up to about 90° C., more preferably up to about 80° C., still more preferably up to about 70° C., even more preferably up to about 65° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

In the present invention, more preferred fatty alcohol is a mixture of cetyl alcohol and stearyl alcohol.

Generally, in the mixture, the weight ratio of cetyl alcohol to stearyl alcohol is preferably from about 1:9 to 9:1, more preferably from about 1:4 to about 4:1, still more preferably from about 1:2.3 to about 1.5:1

Aqueous Carrier

The level and species of the aqueous carrier are selected according to the compatibility with other components, and other desired characteristic of the product.

The carrier useful in the present invention includes water and water solutions of lower alkyl alcohols. The lower alkyl alcohols useful herein are monohydric alcohols having 1 to 6 carbons, more preferably ethanol and isopropanol.

Preferably, the aqueous carrier is substantially water. Deionized water is preferably used. Water from natural sources including mineral cations can also be used, depending on the desired characteristic of the product.

Gel Matrix

Preferably, in the present invention, the cationic surfactant contained in the aqueous base composition, the high melting point fatty compound contained in the aqueous base composition, and an aqueous carrier contained in the aqueous base composition, together form a gel matrix in the aqueous base composition. The gel matrix is suitable for providing various conditioning benefits, such as slippery feel during the application to wet hair and softness and moisturized feel on dry hair.

Preferably, when the gel matrix is formed, the cationic surfactant and the high melting point fatty compound are contained at a level such that the weight ratio of the cationic surfactant to the high melting point fatty compound is in the range of, preferably from about 1:1 to about 1:10, more preferably from about 1:1.5 to about 1:4, still more preferably from about 1:2 to about 1:4, in view of providing improved wet conditioning benefits.

Substantially Free of Detersive Surfactant

The aqueous base composition of the present invention is substantially free of detersive surfactants. The detersive surfactants herein are those selected from anionic surfactants, zwitterionic surfactant, amphoteric surfactant, and combinations thereof.

In the present invention, "the composition being substantially free of detersive surfactants" means that: the aqueous base composition is free of detersive surfactants; or, if the aqueous base composition contains detersive surfactants, the level of such detersive surfactants is very low. In the present invention, a total level of such detersive surfactants, if included, preferably 0.1% or less, more preferably 0.05% or less, still more preferably 0.01% or less by weight of the aqueous base composition. Most preferably, the total level of such detersive surfactants is 0% by weight of the aqueous base composition.

The product composition (comprising the discrete particles of the mixture composition and the aqueous base composition) may also be substantially free of detersive surfactant.

Silicone Compound

Preferably, when contained in the aqueous base composition, the silicone compounds have an average particle size of from about 10 nm to about 100 micron, more preferably from about 0.1 microns to about 100 microns, still more preferably from about 1 microns to about 50 microns, in the aqueous base composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

In some embodiments, amino substituted silicones are preferably used. Preferred aminosilicones include, for example, those which conform to the general formula (I):

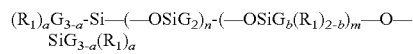

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)CH$_2$—CH$_2$—N($R_2$)$_2$; —N($R_2$)$_2$; —N($R_2$)$_3$A$^-$; —N($R_2$)CH$_2$—CH$_2$—NR$_2$H$_2$A$^-$; wherein $R_2$ is hydrogen, phenyl, benzyl, or a saturated hydrocarbon radical, preferably an alkyl radical from about $C_1$ to about $C_{20}$; A$^-$ is a halide ion.

Highly preferred amino silicones are those corresponding to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Another highly preferred amino silicones are those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

Silicone Polymer Containing Quaternary Groups

Silicone compounds useful herein include, for example, a Silicone Polymer Containing Quaternary Groups comprising terminal ester groups, having a viscosity up to 100,000 mPa·s and a D block length of greater than 200 D units. Without being bound by theory, this low viscosity silicone polymer provides improved conditioning benefits such as smooth feel, reduced friction, and prevention of hair damage, while eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units.

The silicone polymer is present in an amount of from about 0.05% to about 15%, preferably from about 0.1% to about 10%, more preferably from about 0.15% to about 5%, and even more preferably from about 0.2% to about 4% by weight of the composition.

In a preferred embodiment, the polyorganosiloxane compounds have the general formulas (Ia) and (Ib):

M-Y—[-(N$^+$R$_2$-T-N$^+$R$_2$)—Y-]$_m$-[—(NR$^2$-A-E-A'-NR$^2$)—Y-]$_k$-M (Ia)

M-Y—[—(N$^+$R$_2$-T-N$^+$R$_2$)—Y-]$_m$-[—(N$^+$R$^2{}_2$-A-E-A'-N$^+$R$^2{}_2$)—Y-]$_k$-M (Ib)

wherein:
m is >0, preferred 0.01 to 100, more preferred 0.1 to 100, even more preferred 1 to 100, specifically 1 to 50, more specifically 1 to 20, even more specifically 1 to 10,
k is 0 or an average value of from >0 to 50, or preferably from 1 to 20, or even more preferably from 1 to 10,
M represents a terminal group, comprising terminal ester groups selected from
—OC(O)—Z
—OS(O)$_2$—Z
—OS(O$_2$)O—Z
—OP(O)(O—Z)OH
—OP(O)(O—Z)$_2$
wherein Z is selected from monovalent organic residues having up to 40 carbon atoms, optionally comprising one or more hetero atoms.
A and A' each are independently from each other selected from a single bond or a divalent organic group having up to 10 carbon atoms and one or more hetero atoms, and
E is a polyalkylene oxide group of the general formula:

—[CH$_2$CH$_2$O]$_q$—[CH$_2$CH(CH$_3$)O]$_r$—[CH$_2$CH(C$_2$H$_5$)O]$_s$— wherein q=0 to 200, r=0 to 200, s=0 to 200, and q+r+s=1 to 600.
R$^2$ is selected from hydrogen or R,
R is selected from monovalent organic groups having up to 22 carbon atoms and optionally one or more heteroatoms, and wherein the free valencies at the nitrogen atoms are bound to carbon atoms, Y is a group of the formula:

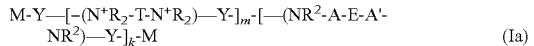  and  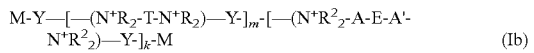 or

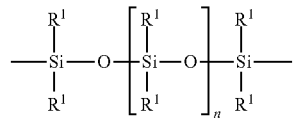

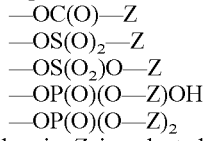

with S=
wherein R1=C$_1$-C$_{22}$-alkyl, C$_1$-C$_{22}$-fluoralkyl or aryl; n=200 to 1000, and these can be identical or different if several S Groups are present in the polyorganosiloxane compound.
K is a bivalent or trivalent straight chain, cyclic and/or branched C$_2$-C$_{40}$ hydrocarbon residue which is optionally interrupted by —O—, —NH—, trivalent N, —NR$^1$—, —C(O)—, —C(S)—, and optionally substituted with —OH, wherein R' is defined as above,
T is selected from a divalent organic group having up to 20 carbon atoms and one or more hetero atoms.

The residues K may be identical or different from each other. In the —K—S—K— moiety, the residue K is bound to the silicon atom of the residue S via a C—Si-bond.

Due to the possible presence of amine groups (—(NR$^2$-A-E-A'-NR$^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}$C-NMR.

In a further embodiment, the polyorganosiloxane composition may comprise:
A) at least one polyorganosiloxane compound, comprising a) at least one polyorganosiloxane group, b) at least one quaternary ammonium group, c) at least one terminal ester group, and d) at least one polyalkylene oxide group (as defined before),
B) at least one polyorganosiloxane compound, comprising at least one terminal ester group, different from compound A).

In the definition of component A) it can be referred to the description of the polyorganosiloxane compounds of the invention. The polyorganosiloxane compound B) differs from the polyorganosiloxane compound A) preferably in that it does not comprise quaternary ammonium groups. Preferred polyorganosiloxane compounds B) result from the reaction of monofunctional organic acids, in particular carboxylic acids, and polyorganosiloxane containing bisepoxides.

In the polyorganosiloxane compositions the weight ratio of compound A) to compound B) is preferably less than 90:10. Or in other words, the content of component B) is at least 10 weight percent. In a further preferred embodiment of the polyorganosiloxane compositions in compound A) the molar ratio of the quaternary ammonium groups b) and the terminal ester groups c) is less than 100:10, even more preferred is less than 100:15 and is most preferred less than 100:20.

The silicone polymer has a viscosity at 20° C. and a shear rate of 0.1 s$^{-1}$ (plate-plate system, plate diameter 40 mm, gap width 0.5 mm) of less than 100,000 mPa·s (100 Pa·s). In further embodiments, the viscosities of the neat silicone polymers may range from 500 to 100,000 mPa·s, or preferably from 500 to 70,000 mPa·s, or more preferably from 500 to 50,000 mPa·s, or even more preferably from 500 to 20,000 mPa·s. In further embodiments, the viscosities of the neat polymers may range from 500 to 10,000 mPa·s, or preferably 500 to 5000 mPa·s determined at 20° C. and a shear rate of 0.1 s$^{-1}$.

In addition to the above listed silicone polymers, the following preferred compositions are provided below. For example, in the polyalkylene oxide group E of the general formula:

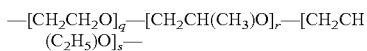
—[CH$_2$CH$_2$O]$_q$—[CH$_2$CH(CH$_3$)O]$_r$—[CH$_2$CH(C$_2$H$_5$)O]$_s$— wherein the q, r, and s indices may be defined as follows:
q=0 to 200, or preferably from 0 to 100, or more preferably from 0 to 50, or even more preferably from 0 to 20,
r=0 to 200, or preferably from 0 to 100, or more preferably from 0 to 50, or even more preferably from 0 to 20,
s=0 to 200, or preferably from 0 to 100, or more preferably from 0 to 50, or even more preferably from 0 to 20, and
q+r+s=1 to 600, or preferably from 1 to 100, or more preferably from 1 to 50, or even more preferably from 1 to 40.

For polyorganosiloxane structural units with the general formula S:

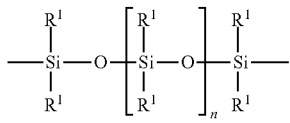

R$^1$=C$_1$-C$_{22}$-alkyl, C$_1$-C$_{22}$-fluoralkyl or aryl; n=from 200 to 1000, or preferably from 300 to 500, K (in the group —K—S—K—) is preferably a bivalent or trivalent straight chain, cyclical or branched C$_2$-C$_{20}$ hydrocarbon residue which is optionally interrupted by —O—, —NH—, trivalent N, —NR$^1$—, —C(O)—, —C(S)—, and optionally substituted with —OH.

In specific embodiments, IV is C$_1$-C$_{18}$ alkyl, C$_1$-C$_{18}$ fluoroalkyl and aryl. Furthermore, IV is preferably C$_1$-C$_{18}$ alkyl, C$_1$-C$_6$ fluoroalkyl and aryl. Furthermore, R$^1$ is more preferably C$_1$-C$_6$ alkyl, C$_1$-C$_6$ fluoroalkyl, even more preferably C$_1$-C$_4$ fluoroalkyl, and phenyl. Most preferably, R$^1$ is methyl, ethyl, trifluoropropyl and phenyl.

As used herein, the term "C$_1$-C$_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "C$_1$-C$_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term "aryl" means unsubstituted or phenyl substituted once or several times with OH, F, Cl, CF$_3$, C$_1$-C$_6$ alkyl, C$_1$-C$_6$ alkoxy, C$_3$-C$_7$ cycloalkyl, C$_2$-C$_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from C$_1$-C$_{300}$ carboxylic acids, for example acetate, propionate, octanoate, especially from C$_{10}$-C$_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

In a preferred embodiment the polyorganosiloxane compounds are of the general formulas (Ia) and (Ib):

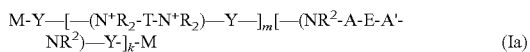
M-Y—[—(N$^+$R$_2$-T-N$^+$R$_2$)—Y—]$_m$[—(NR$^2$-A-E-A'-NR$^2$)—Y-]$_k$-M (Ia)

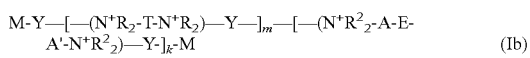
M-Y—[—(N$^+$R$_2$-T-N$^+$R$_2$)—Y—]$_m$—[—(N$^+$R$^2$$_2$-A-E-A'-N$^+$R$^2$$_2$)—Y-]$_k$-M (Ib)

wherein each group is as defined above; however, the repeating units are in a statistical arrangement (i.e., not a block-wise arrangement).

In a further preferred embodiment the polyorganosiloxane compounds may be also of the general formulas (IIa) or (IIb):

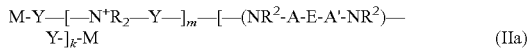
M-Y—[—N$^+$R$_2$—Y—]$_m$—[—(NR$^2$-A-E-A'-NR$^2$)—Y-]$_k$-M (IIa)

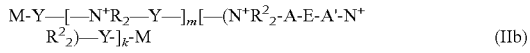
M-Y—[—N$^+$R$_2$—Y—]$_m$[—(N$^+$R$^2$$_2$-A-E-A'-N$^+$R$^2$$_2$)—Y-]$_k$-M (IIb)

wherein each group is as defined above. Also in such formula the repeating units are usually in a statistical arrangement (i.e. not a block-wise arrangement).

wherein, as defined above, M is
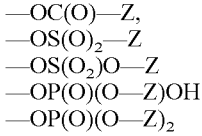
—OC(O)—Z,
—OS(O)$_2$—Z
—OS(O$_2$)O—Z
—OP(O)(O—Z)OH
—OP(O)(O—Z)$_2$ Z is a straight chain, cyclic or branched saturated or unsaturated C$_1$-C$_{20}$, or preferably C$_2$ to C$_{18}$, or even more preferably a hydrocarbon radical, which can be interrupted by one or more —O—, or —C(O)— and substituted with —OH. In a specific embodiment, M is —OC(O)—Z resulting from normal carboxylic acids in particular with more than 10 carbon atoms like for example dodecanoic acid.

In a further embodiment, the molar ratio of the polyorganosiloxane-containing repeating group —K—S—K— and the polyalkylene repeating group -A-E-A'- or -A'-E-A- is between 100:1 and 1:100, or preferably between 20:1 and 1:20, or more preferably between 10:1 and 1:10.

In the group —(N$^+$R$_2$-T-N$^+$R$_2$)—, R may represent a monovalent straight chain, cyclic or branched C$_1$-C$_{20}$ hydrocarbon radical, which can be interrupted by one or more —O—, —C(O)— and can be substituted by —OH, T may represent a divalent straight-chain, cyclic, or branched C$_1$-C$_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Additional Components

The aqueous base composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; ultraviolet and infrared screening and absorbing agents such as benzophenones; and antidandruff agents such as zinc pyrithione.

Method of Preparation of Product Compositions

The product composition of the present invention can be prepared by, for example, below METHOD A or METHOD B.

Method A

The product composition of the present invention can be prepared, for example, by the following method (hereinafter METHOD A) comprising the steps of:

Preparing a mixture composition comprising a surfactant and a high melting point fatty compound and a benefit agent;

Separately preparing an aqueous base composition comprising a surfactant, a high melting point fatty compound, and an aqueous carrier, and wherein the aqueous base composition is substantially free of detersive surfactant;

Mixing the mixture composition and the aqueous base composition, to form a discrete particle of the mixture composition dispersed in the aqueous base composition.

Preferably, when mixed, the mixture composition and the aqueous base composition respectively have a temperature lower than the melting point of the high melting point fatty compound.

Preferably, when mixed, the mixture composition has a temperature lower than the melting point of the high melting point fatty compound contained in the mixture composition, and the mixture composition has such temperature during and after mixing with the aqueous base composition. Also preferably, the aqueous base composition also has a temperature lower than the melting point of the high melting point fatty compound contained in the mixture composition when mixed with the mixture composition, and has such temperature during and after mixing with the mixture composition.

Thus, when mixed, the mixture composition and the aqueous base composition respectively have a temperature of preferably at least 2° C. lower, more preferably at least 5° C. lower, still more preferably at least 10° C. lower, even more preferably at least 15° C. lower than the above melting point of the high melting point fatty compound.

It is also preferred that, when mixed, the mixture composition and the aqueous base composition respectively have a temperature of from about 0° C. to about 50° C., more preferably from about 10° C. to about 40° C., still more preferably from about 15° C. to about 35° C.

Method B

Alternatively, the product composition of the present invention can be prepared by the following method (hereinafter METHOD B) comprising the steps of:

Preparing a discrete particle of a mixture composition wherein the mixture composition comprises a surfactant and a high melting point fatty compound and a benefit agent;

Separately preparing an aqueous base composition comprising a surfactant, a high melting point fatty compound, and an aqueous carrier, and wherein the aqueous base composition is substantially free of detersive surfactant;

Mixing the discrete particle and the aqueous base composition, to disperse discrete particle in the aqueous base composition.

In this METHOD B, the discrete particle may be preferably solid.

In METHOD B, a solvent or carrier may be used to prepare discrete particle of the mixture composition. Such solvents and carriers are considered as components of the aqueous base composition when calculating the amounts of components.

Preferably, when mixed, the discrete particle and the aqueous base composition respectively have a temperature lower than the melting point of the high melting point fatty compound.

Preferably, when mixed, the discrete particle has a temperature lower than the melting point of the high melting point fatty compound contained in the discrete particle, and the discrete particle has such temperature during and after mixing with the aqueous base composition. Also preferably, the aqueous base composition also has a temperature lower than the melting point of the high melting point fatty compound contained in the discrete particle when mixed with the discrete particle, and has such temperature during and after mixing with the discrete particle.

Thus, when mixed, the discrete particle and the aqueous base composition respectively have a temperature of preferably at least 2° C. lower, more preferably at least 5° C. lower, still more preferably at least 10° C. lower, even more preferably at least 15° C. lower than the above melting point of the high melting point fatty compound.

It is also preferred that, when mixed, the discrete particle and the aqueous base composition respectively have a temperature of from about 0° C. to about 50° C., more preferably from about 10° C. to about 40° C., still more preferably from about 15° C. to about 35° C.

Preparation of the Mixture Composition

Both in METHOD A and B, preferably, the mixture composition is prepared by steps of: preparing a melting mixture composition comprising the surfactant and the high melting point fatty compound, wherein the temperature of the melting mixture composition is higher than the melting point of the high melting point fatty compound contained in the mixture composition; cooling the melting mixture composition to a temperature which is lower than the melting point of the high melting point fatty compound contained in the mixture composition, to form the mixture composition. In METHOD B, the discrete particle can be prepared concurrently when preparing the mixture composition during the above cooling step, or can be prepared after forming the mixture composition.

Preferably, the temperature of the melting mixture composition is at least 2° C., still more preferably at least 5° C., even more preferably at least 10° C. higher than the above melting point of the high melting point fatty compound. It is also preferred that the temperature of the melting mixture composition is from about 30° C. to about 150° C., more preferably from about 40° C. to about 100° C., still more preferably from about 50° C. to about 95° C., even more preferably from about 55° C. to about 90° C., further more preferably from about 66° C. to about 90° C.

Preferably, the melting mixture composition is cooled to a temperature which is lower than a melting point of the high melting point fatty compound contained in the mixture composition, more preferably at least 2° C., more preferably at least 5° C., still more preferably at least 10° C. lower than the melting point of the high melting point fatty compound contained in the mixture composition. It is also preferred that the melting mixture composition is cooled to a temperature of from about −200° C. to about 50° C., more preferably from about −40° C. to about 50° C., still more preferably from about 0° C. to about 30° C.

When Containing the Benefit Agents in the Mixture Composition When the mixture composition further comprises the benefit agents, the mixture composition can be prepared by steps of:

Preparing a melting mixture composition comprising the surfactant and the high melting point fatty compound, wherein the temperature of the melting mixture composition is higher than a melting point of the high melting point fatty compound contained in the mixture composition; cooling the melting mixture composition to the temperature which is lower than a melting point of the high melting point fatty compound contained in the mixture composition, to form the mixture composition, wherein the benefit agent can be added anytime depending on the properties of the benefit agent, for example, the benefit agent can be added to the mixture composition before cooling, during cooling especially when using volatile benefit agent such as perfumes, or after cooling preferably right after cooling such as within 30 min after cooling.

When the mixture composition comprises a benefit agent, the benefit agent can be homogeneously mixed with the mixture composition, and homogeneous discrete particles can be formed in the compositions. Alternatively, in the discrete particle, the benefit agent can form an inner core covered by an outer shell formed by the mixture composition.

When Containing the Benefit Agent in the Aqueous Base Composition

When the aqueous base composition comprises a benefit agent, the benefit agent can be homogeneously mixed with the aqueous base composition.

When the aqueous base composition comprises a benefit agent, the benefit agent can be added to the aqueous base composition anytime, for example, before adding the mixture composition and/or the discrete particle, after adding the mixture composition and/or the discrete particle, and/or concurrently with the discrete particle.

Examples

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Product Compositions—S

|  |  | Wt % in the product composition | | | |
|---|---|---|---|---|---|
|  |  | Ex. S-1 | Ex. S-2 | CEx. S-i | CEx. S-ii |
| Aqueous base composition | Cetyl alcohol | 0.4 | 0.4 | 1.0 | 1.0 |
|  | Stearyl alcohol | 1.0 | 1.0 | 2.5 | 2.5 |
|  | BTMS/IPA *1 | 1.2 | 1.2 | 3.0 | 3.0 |
|  | Disodium EDTA | 0.05 | 0.05 | 0.13 | 0.13 |
|  | Benzyl Alcohol | 0.16 | 0.16 | 0.4 | 0.4 |
|  | Kathon CG | 0.01 | 0.01 | 0.03 | 0.03 |
|  | Water | q.s. to 100% | q.s. to 100% | q.s. to 100% | q.s. to 100% |
|  | Aminosilicone *2 | — | — | 0.45 | — |
|  | Quaternized aminosilione *3 | — | — | — | 0.45 |
| Mixture composition-1 | Mixture composition including Aminosilicone*2, having the following composition: (wt % in the mixture composition) | 4.54 | — | — | — |
|  | Cetyl alcohol 14.0 |  |  |  |  |
|  | Stearyl alcohol 35.0 |  |  |  |  |
|  | BTMS/IPA *1 41.0 |  |  |  |  |
|  | Aminosilicone *2 10.0 |  |  |  |  |
| Mixture composition-2 | Mixture composition including Quaternized aminosilione *3 having the following composition | — | 4.54 | — | — |

-continued

|  |  | Wt % in the product composition | | | |
|---|---|---|---|---|---|
|  |  | Ex. S-1 | Ex. S-2 | CEx. S-i | CEx. S-ii |
|  | (wt % in the mixture composition) | | | | |
| Cetyl alcohol | 14.0 | | | | |
| Stearyl alcohol | 35.0 | | | | |
| BTMS/IPA *1 | 41.0 | | | | |
| Quaternized aminosilione *3 | 10.0 | | | | |
| Particle size of Discrete particle, before mixing with the aqueous base composition | | 300-500 micrometer | | n/a | n/a |
| Discrete particle | | Swollen discrete particle of the mixture composition is dispersed in the aqueous base composition and observed in the product composition by microscope for at least 18 months. The swollen discrete particles do not show maltese cross when measured by polarized microscope. The swollen discrete particle is not water-in-oil or water-in-oil-in-water emulsion. | | n/a | n/a |
| Silicone deposition evenness at 1 months | | 2.1 | 1.6 | 3.0 | 3.5 |

Product Compositions—S-Cont.

|  |  | Wt % in the product composition | | |
|---|---|---|---|---|
|  |  | Ex. S-3 | Ex. S-4 | CEx. S-iii |
| Aqueous base composition | Cetyl alcohol | 1.0 | 0.8 | 1.2 |
| | Stearyl alcohol | 1.0 | 1.9 | 3.0 |
| | BTMS/IPA *1 | 1.0 | 1.9 | 3.0 |
| | Disodium EDTA | 0.05 | 0.05 | 0.13 |
| | Benzyl Alcohol | 0.16 | 0.16 | 0.4 |
| | Kathon CG | 0.01 | 0.01 | 0.03 |
| | Water | q.s. to 100% | q.s. to 100% | q.s. to 100% |
| | Aminosilicone *2 | — | — | — |
| | Quaternized aminosilione *3 | — | — | 1.0 |
| Mixture composition-3 | Mixture composition including Quaternized aminosilione *3, having the following composition: | 5.0 | — | — |
| | (wt % in the mixture composition) | | | |
| | Cetyl alcohol | 12.4 | | | |
| | Stearyl alcohol | 31.1 | | | |
| | BTMS/IPA *1 | 36.5 | | | |
| | Quaternized aminosilione *3 | 20.0 | | | |
| Mixture composition-4 | Mixture composition including Quaternized aminosilione *3 having the following composition | — | 3.3 | — |
| | (wt % in the mixture composition) | | | |
| | Cetyl alcohol | 10.9 | | | |
| | Stearyl alcohol | 27.2 | | | |
| | BTMS/IPA *1 | 31.9 | | | |
| | Quaternized aminosilione *3 | 30.0 | | | |
| Particle size of Discrete particle, before mixing with the aqueous base composition | | 1.2 mm | | n/a |
| Discrete particle | | Swollen discrete particle of the mixture composition is dispersed in the aqueous base composition and observed in the product composition by microscope for at least 18 months. The swollen | | n/a |

-continued

|  | Wt % in the product composition | | |
|---|---|---|---|
|  | Ex. S-3 | Ex. S-4 | CEx. S-iii |
|  | discrete particles do not show maltese cross when measured by polarized microscope. The swollen discrete particle is not water-in-oil or water-in-oil-in-water emulsion. | | |
| Silicone deposition evenness at 1 months | 2.03 | 2.06 | 3.45 |

Product Composition—M

| | | Wt % in the product composition | |
|---|---|---|---|
| | | Ex. M-1 | CEx. M-i |
| Aqueous base composition | Cetyl alcohol | 1.2 | 1.2 |
| | Stearyl alcohol | 3.0 | 3.0 |
| | BTMS/IPA *1 | 2.2 | 2.2 |
| | Dicetyl dimethyl Ammonium Chloride | 0.5 | 0.5 |
| | Disodium EDTA | 0.13 | 0.13 |
| | Benzyl Alcohol | 0.4 | 0.4 |
| | Kathon CG | 0.03 | 0.03 |
| | Water | q.s. to 100% | q.s. to 100% |
| | Aminosilicone * 1 | 1.5 | 1.5 |
| | Mica | — | 0.24 |
| Mixture composition | Mixture composition including mica, having the following composition | 3.84 | — |
| | (w % in the mixture composition) | | |
| | Cetyl alcohol 11.7 | | |
| | Stearyl alcohol 29.1 | | |
| | BTMS/IPA *1 34.1 | | |
| | Mica 25.1 | | |
| Particle size of Discrete particle, before mixing with the aqueous base composition | | 200-300 micrometers | n/a |
| Discrete particle | | Swollen Discrete particle of the mixture composition is dispersed in the aqueous base composition and observed in the product composition by microscope for at least 18 months. The swollen discrete particles do not show maltese cross when measured by polarized microscope. The swollen discrete particle is not water-in-oil or water-in-oil-in-water emulsion. | n/a |
| Agglomeration/Residue | | Significant reduction of mica agglomeration and mica residue, compared to CEx. M-i. Almost no visible mica agglomeration is observed in the product composition even after 18 months and almost no mica residues are observed in the equipment for mixing the discrete particle and the aqueous base composition, and afterwards | Visible mica agglomerations are observed in the product composition, and mica residues are observed in the manufacturing equipment. |

Product Compositions—P

| | | Wt % in the product composition | |
|---|---|---|---|
| | | Ex. P-1 | Ex. P-2 |
| Aqueous base composition | Cetyl alcohol | 1.0 | 1.0 |
| | Stearyl alcohol | 2.5 | 2.5 |
| | BTMS/IPA *1 | 3.0 | 3.0 |
| | Disodium EDTA | 0.13 | 0.13 |
| | Benzyl Alcohol | 0.4 | 0.4 |
| | Kathon CG | 0.03 | 0.03 |
| | Water | q.s. to 100% | q.s. to 100% |
| | Green Dye (mixture of Blue 1 + Yellow 5 + DI water) | — | 0.8 |
| Mixture composition-1 | Mixture composition including Red pigment, having the following composition | 0.4 | — |
| | (w % in the mixture composition) | | |
| | Cetyl alcohol | 15.5 | |
| | Stearyl alcohol | 38.5 | |
| | BTMS/IPA *1 | 45.0 | |
| | Pigment (OTS-2-RED-516P) | 1 | |
| Mixture composition-2 | Mixture composition including Black pigment, having the following composition | — | 0.2 |
| | (w % in the mixture composition) | | |
| | Cetyl alcohol | 15.5 | |
| | Stearyl alcohol | 38.5 | |
| | BTMS/IPA *1 | 45.0 | |
| | Pigment (OTS-2-BLACK-BL100P) | 1 | |
| Particle size of Discrete particle, before mixing with the aqueous base composition | | 300-500 micrometers | |
| Discrete particle | | Swollen Discrete particle of the mixture composition is dispersed in the aqueous base composition and observed in the product composition by microscope for at least 18 months. The swollen discrete particles do not show maltese cross when measured by polarized microscope. The swollen discrete particle is not water-in-oil or water-in-oil-in-water emulsion. | |
| Aesthetics at 18 months | | The discrete particles are observed in the product composition as red-colored dispersions | The discrete particles are observed in the product composition as black-colored dispersions |

Product Compositions—C

| | | Wt % in the product composition Ex. C-1 |
|---|---|---|
| Aqueous base composition | Cetyl alcohol | 1.2 |
| | Stearyl alcohol | 2.9 |
| | BTMS/IPA *1 | 3.0 |
| | Disodium EDTA | 0.13 |
| | Benzyl Alcohol | 0.4 |
| | Kathon CG | 0.03 |
| | Water | q.s. to 100% |
| | Aminosilicone *2 | 3.5 |
| Mixture composition-1 | Mixture composition including Charcoal, having the following composition | 0.2 |
| | (w % in the mixture composition) | |

-continued

|  |  | Wt % in the product composition Ex. C-1 |
|---|---|---|
|  | Cetyl alcohol 15.0 |  |
|  | Stearyl alcohol 37.0 |  |
|  | BTMS/IPA *1 43.0 |  |
|  | Charcoal 5.0 |  |
| Particle size of Discrete particle, before mixing with the aqueous base composition |  | 0.75 mm |
| Discrete particle |  | Swollen Discrete particle of the mixture composition is dispersed in the aqueous base composition and observed in the product composition by microscope for at least 18 months. The swollen discrete particles do not show maltese cross when measured by polarized microscope. The swollen discrete particle is not water-in-oil or water-in-oil-in-water emulsion. |
| Cleanness in manufacturing equipment |  | Almost no charcoal residues are observed in the equipment for mixing the discrete particle and the aqueous base composition, and afterwards |
| Aesthetics at 18 months |  | The discrete particles are observed in the product composition as black-colored dispersions |

Product Compositions—SA

|  |  | Wt % in the product composition | | |
|---|---|---|---|---|
|  |  | Ex. SA-1 | Ex. SA-2 | CEx. SA-i |
| Aqueous base composition | Cetyl alcohol | 0.38 | 0.38 | 1.2 |
|  | Stearyl alcohol | 0.9 | 0.9 | 3.0 |
|  | BTMS/IPA *1 | 0.96 | 0.96 | 3.0 |
|  | Disodium EDTA | 0.04 | 0.04 | 0.17 |
|  | Benzyl Alcohol | 0.13 | 0.13 | 0.4 |
|  | Kathon CG | 0.01 | 0.01 | 0.03 |
|  | Water | q.s. to 100% | q.s. to 100% | q.s. to 100% |
|  | Salicylic acid | — | — | 2.0 |
|  | Quaternized aminosilione *3 | — | — | 3.5 |
| Mixture composition-1 | Mixture composition including Salicylic acid, having the following composition: | 17.8 | — | — |
|  | (wt % in the mixture composition) |  |  |  |
|  | Cetyl alcohol 28.9 |  |  |  |
|  | Stearyl alcohol 19.9 |  |  |  |
|  | BTMS/IPA *1 17.7 |  |  |  |
|  | Stearamidopropyl Dimethylamine 11.0 |  |  |  |
|  | Salicylic acid 22.5 |  |  |  |
| Mixture composition-2 | Mixture composition including Salicylic acid, having the following composition | — | 13.4 | — |
|  | (wt % in the mixture composition) |  |  |  |
|  | Cetyl alcohol 26.0 |  |  |  |
|  | Stearyl alcohol 18.0 |  |  |  |
|  | BTMS/IPA *1 16.0 |  |  |  |
|  | Stearamidopropyl Dimethylamine 10.0 |  |  |  |
|  | Salicylic acid 30.0 |  |  |  |
| Particle size of Discrete particle, before mixing with the aqueous base composition |  | 1.2 mm |  | n/a |

|  | Wt % in the product composition | | |
|---|---|---|---|
|  | Ex. SA-1 | Ex. SA-2 | CEx. SA-i |
| Discrete particle | Swollen discrete particle of the mixture composition is dispersed in the aqueous base composition and observed in the product composition by microscope for at least 3 months. The swollen discrete particles do not show maltese cross when measured by polarized microscope. The swollen discrete particle is not water-in-oil or water-in-oil-in-water emulsion. | | n/a |
| Crystallization at 3 months | No needle like crystallization of Salicylic acid is observed in the aqueous base composition. | | Needle like crystallization of Salicylic acid is observed in the aqueous base composition, which is not desirable for texture and human safety. |

Product Compositions—CEx.

|  |  | Wt % in the product composition CEx. i |
|---|---|---|
| Aqueous base composition | Water | q.s. to 100% |
| Mixture composition | Mixture composition having the following composition | |
|  |  | Wt % in the mixture composition |
|  | BTMS/IPA *1 | 45.6 |
|  | Cetyl Alcohol | 15.5 |
|  | Stearyl alcohol | 38.9 |
|  |  | 6.86 |
| Particle size of Discrete particle, before mixing with the aqueous base composition |  | 1 mm |
| Discrete particle |  | Discrete particles of the mixture composition are diffused and collapsing in the aqueous base composition and NOT observed in the product composition by microscope within 1 week |

Definitions of Components
1 BTMS/IPA: 80% of Behenyl Trimethyl Ammonium Methosulfate and 20% of Isopropyl alcohol
2 Aminosilicone: Available from Momentive having a viscosity 10,000 mPa·s, and having following formula (I):

$$(R_1)_a G_{3-a}\text{-Si}-(-OSiG_2)_n-(-OSiG_b(R_1)_{2-b})_m-O-SiG_{3-a}(R_1)_a \quad (I)$$

wherein G is methyl; a is an integer of 1; b is 0, 1 or 2, preferably 1; n is a number from 400 to about 600; m is an integer of 0; $R_1$ is a monovalent radical conforming to the general formula $C_qH_{2q}L$, wherein q is an integer of 3 and L is $-NH_2$ 3 Quaternized aminosilicone: Available from Momentive having the following formula:

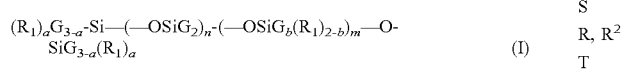

wherein

| M | lauric ester |
|---|---|
| Y | K—S—K |
| K | $CH_2-CHOH-CH_2-O-C_3H_6$ |
| S | PDMS block with 368 siloxane units |
| R, $R^2$ | Methyl |
| T | $C_6H_{12}$ |
| A | $CH_2-COO-$ |
| A' | $CO-CH_2$ |
| E | Ethylene oxide $(CH_2-CH_2-O)$ with average degree of ethoxylation of 2 |
| Ratio of silicone blocks:alkylene oxide blocks | 1:1 |
| Total Viscosity | 4700 mPa · s |

Method of Preparation of the Product Composition

The embodiments disclosed and represented by "Ex." are hair conditioning product compositions of the present invention, and were prepared by Method B explained above, and the following in more detail:

Preparing the mixture composition comprising the surfactant and the high melting point fatty compound and benefit agent, wherein the mixture composition was prepared by the following method:
- Preparing a melting mixture composition wherein the temperature of the melting mixture composition is higher than a melting point of the high melting point fatty compound contained in the mixture composition, i.e., from about 66° C. to about 90° C.;
- Cooling the melting mixture composition to a temperature which is lower than a melting point of the high melting point fatty compound contained in the mixture composition, i.e., from about 0° C. to about 40° C., to form the mixture composition.

Preparing a solid discrete particle consisting of the mixture composition;

Separately preparing an aqueous base composition;

Mixing the discrete particle and the aqueous base composition, both having a temperature lower than a melting point of the high melting point fatty compound contained in the mixture composition, i.e., from about 10° C. to about 40° C., so that the discrete particle is dispersed in the aqueous base composition.

Discrete particles are swollen in the product composition. The hair conditioner product compositions disclosed and represented by "CEx." are comparative examples, and were prepared by either the above METHOD B when the compositions contain discrete particles or a conventional method when the compositions do not contain discrete particles.

Properties and Conditioning Benefits

For some of the above compositions, properties and conditioning benefits are evaluated by the following methods. Results of the evaluation are also shown above.

The embodiments disclosed and represented by "Ex." are hair conditioning product compositions of the present invention which are particularly useful for rinse-off use, and have many advantages. For example, the product composition of the present invention provides at least one the followings: more flexibility in the product composition rheology; improved stability in the product composition; improved deposition of benefit agents; and improved visual/aesthetic appearance. Some of such benefits can be understood by the comparison with comparative examples "CEx.".

For example, the product compositions of the present invention "Ex. 5-1" and "Ex. S-2" provide improved deposition of silicones, especially improved evenness compared to the comparative examples "CEx.S-i" and "CEx.S-ii".

For example, the product composition of the present invention "Ex. M-1" provides improved stability and thus provide reduced agglomerations and residues, compared to the comparative example "CEx.M-i".

For example, the product compositions of the present invention "Ex. P-1" and "Ex. P-2" and "Ex. C-1" provide improved aesthetics by colored dispersions.

For example, the product compositions of the present invention "Ex. SA-1" and "Ex. SA-2" improved stability and thus provide reduced crystallization in the aqueous base composition, compared to the comparative example "CEx.SA-i".

Silicone Deposition Evenness

Silicone deposition evenness value is a comparison between a silicone deposition amount at damaged hair switch (representing hair tips) and a silicone deposition amount at the undamaged hair switch (representing hair roots). Generally, hair tips are more damaged compared to hair roots then may need more silicone deposition. However, silicones tend to deposit more on hair roots than hair tips and it has been difficult to obtain balanced silicone deposition at roots and tips of hairs, i.e., silicone deposition evenly on hair roots and tips.

Silicone deposition evenness value herein are measured by the following steps:

Silicone deposition amounts herein are measured by a method consisting of: (i) a preparation of hair switch; and (ii) silicone deposition measurement, and (iii) evaluation.

(i) Preparation of Hair Switch

Undamaged hair switches are made by non-permed and non-colored/bleached hair.

Damaged hair switches are prepared by (1) bleaching the undamaged hair switches in oxidation agent (chemical damage), (2) wash off the chemicals completely and (3) combing the hair switches to get mechanical damages.

For the silicone deposition measurement, 2 gram hair switches (damaged and undamaged) with a length of 6 inches are used. The hair switches are prepared by following steps:
(1) Applying 0.2 g of non-conditioning shampoo per one hair switch, lathering, rinsing and drying the hair switches;
(2) Applying a non-conditioning shampoo at a level of 0.2 cc per one hair switch and lathering the hair switch; and rinsing the hair switch;
(3) Repeating (2);
(4) Repeating (2) again;
(5) Rinsing the hair switch and then drying the hair switch.

The hair switch is ready for the measurement of its silicone deposition amount, and evaluation.

(ii) Silicone Deposition Measurement

The deposited silicone on the hair switch is extracted in an appropriate solvent. The extracts are then introduced into an atomic absorption/emission detector instrument and measured at the appropriate wavelength. The absorbance/emission value returned by the instrument is then converted to actual concentration (microgram) of silicone compound deposited on the hair through an external calibration curve obtained with known weights of a well characterized standard of the silicone compound under study. Microgram (g) per gram on hair is calculated.

(iii) Evaluation

The above deposition measurements in the step (ii) are conducted on at least 3 different hair switches prepared by the step (i) per one conditioner, and then calculate an average of "Microgram (μg) per gram" for damaged and undamaged hair switches respectively. The average of "Microgram (μg) per gram" for the damaged hair switches is divided by the average of "Microgram (u g) per gram" for the undamaged hair switches, to obtain Silicone deposition evenness value.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioning product composition comprising:
a discrete particle of a mixture composition, wherein the mixture composition comprises a surfactant wherein the surfactant is selected from the group consisting of behenyl trimethyl ammonium methosulfate, behenyl trimethyl ammonium chloride, stearamidopropyl dimethylamine, and mixtures thereof, a high melting point fatty compound wherein the high melting point fatty compound is selected from the group consisting of cetyl alcohol, stearyl alcohol and mixtures thereof and a benefit agent wherein the benefit agent is a coloring agents to add a different color to the discrete particle from the color of the aqueous base composition;
an aqueous base composition comprising a surfactant, a high melting point fatty compound;
and an aqueous carrier, wherein the aqueous base composition is substantially free of a detersive surfactant selected from anionic surfactants, zwitterionic surfactant, amphoteric surfactant, and combinations thereof.

2. The hair conditioning product composition of claim 1, wherein the discrete particle exists in the composition for 1 month or longer.

3. The hair conditioning product composition of claim 1, wherein the discrete particle is swollen in the product composition.

4. The hair conditioning product composition of claim 1, wherein the discrete particle is not an oil-in-water emulsion or water-in-oil-in-water emulsion.

5. The hair conditioning product composition of claim 1, wherein the discrete particle before swelling is solid.

6. The hair conditioning product composition of claim 1, wherein the discrete particle before swelling contains less than about 50% of water, by weight of the discrete particle.

7. The hair conditioning product composition of claim 1, wherein the discrete particle before swelling comprises from about 10% to about 100% of the surfactants and the high melting point fatty compounds, by weight of the discrete particle.

8. The hair conditioning product composition of claim 1, wherein the surfactant contained in the aqueous base composition is hydrophobic.

9. The hair conditioning product composition of claim 1, wherein the surfactant contained in the aqueous base composition is selected from the group consisting of: a cationic surfactant, a nonionic surfactant, and mixtures thereof.

10. The hair conditioning product composition of claim 1, wherein the surfactant contained in the discrete particle is hydrophobic.

11. The hair conditioning product composition of claim 1, wherein the surfactant contained in the discrete particle is selected from the group consisting of: a cationic surfactant, a nonionic surfactant, and mixtures thereof.

\* \* \* \* \*